United States Patent
Core et al.

(10) Patent No.: US 8,315,356 B2
(45) Date of Patent: Nov. 20, 2012

(54) IMAGE ALIGNMENT

(75) Inventors: Matthew Core, San Jose, CA (US); Paul Vander Griend, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 245 days.

(21) Appl. No.: 12/884,515

(22) Filed: Sep. 17, 2010

(65) Prior Publication Data
US 2012/0069968 A1      Mar. 22, 2012

(51) Int. Cl.
*A61N 5/10*     (2006.01)
*A61B 6/08*     (2006.01)

(52) U.S. Cl. ................... 378/65; 378/205; 378/206
(58) Field of Classification Search ............ 378/62, 378/65, 205–209, 901
See application file for complete search history.

(56) References Cited

U.S. PATENT DOCUMENTS

| | | | |
|---|---|---|---|
| 6,961,405 B2 * | 11/2005 | Scherch | 378/65 |
| 7,894,649 B2 * | 2/2011 | Fu et al. | 382/128 |
| 2005/0085710 A1 | 4/2005 | Earnst et al. | |
| 2005/0228255 A1 | 10/2005 | Saracen et al. | |
| 2005/0234327 A1 | 10/2005 | Saracen et al. | |
| 2006/0274885 A1 * | 12/2006 | Wang et al. | 378/65 |

OTHER PUBLICATIONS

"Treatment Delivery Manual", Accuray Incorporated, CyberKnife® System, P/N 029574B-ENG, 2009, pp. i, ii, 7-16 through 7-49.
Coste-Manière, È. et al., "Robotic whole body stereotactic radiosurgery: clinical advantages of the CyberKnife® integrated system", The International Journal of Medical Robotics +Computer Assisted Surgery, 2005, www.roboticpublications.com, pp. 28-39.

* cited by examiner

*Primary Examiner* — Irakli Kiknadze
(74) *Attorney, Agent, or Firm* — Lowenstein Sandler PC

(57) ABSTRACT

A method and apparatus for positioning a patient for radiation treatment are described. The method includes obtaining a plurality of projection images of a patient positioned on a treatment couch, displaying at least one of the plurality of projection images with a corresponding synthetic projection image on a display, adjusting the position of the at least one projection image on the display to approximately align with the corresponding synthetic projection image in response to a user dragging the at least one projection image on the display with a user interface device, and moving the treatment couch to position the patient based on position adjustments of the at least one projection image.

20 Claims, 10 Drawing Sheets

IMAGE ALIGNMENT

TECHNICAL FIELD

Embodiments of the present invention relate generally to radiation treatment systems and, more particularly, the use of alignment of images to position a patient in a radiation treatment system.

BACKGROUND

In order to deliver effective patient treatment, radiation treatment systems require that the patient be properly positioned in relation to the system that is to deliver the treatment. Current treatment delivery systems utilize algorithms that automatically align a treatment couch to properly position a patient relative to the treatment delivery system. However, because some algorithms may only be capable of making fine adjustments to the position of the patient, the initial position of the treatment couch (and the patient) is often so out of alignment with the imaging center that it prevents the algorithm from returning a useful result. In these cases, a user of the treatment delivery system must manually adjust the position of the couch to more closely align with the imaging center. In order to accomplish this, current solutions acquire a pair of initial projection images of the patient and display them in conjunction with a corresponding pair of synthetic projection images. The user then adjusts the position of the projection images to overlay the synthetic projection images, and the system moves the treatment couch accordingly. By doing this, the patient is eventually moved close enough to a position that allows the algorithm to properly detect the position of the patient in relation to the imaging center.

FIG. 1 illustrates a user interface 100 for adjusting the position of a projection image that is currently used in the CyberKnife® radiosurgery system, developed by Accuray, Incorporated of California. The user interface 100 includes three sliders 104 to allow the user to move projection images 102 relative to the synthetic projection images 106. The position of each projection image relative to the synthetic projection images can be seen in overlay windows 108. Changing the position of one of the sliders 104 simulates a change in the position of the treatment couch in a particular direction relative to anatomical coordinates of the human body (inferior/superior, left/right, and anterior/posterior, respectively). This change is reflected in a shift in the position of the projection images in overlay windows 108. Because the displayed projection images are two dimensional projections of a three dimensional figure, the user must identify how the projection images will respond to movements of the sliders, which allow for movements in three directions.

BRIEF DESCRIPTION OF THE DRAWINGS

The present invention is illustrated by way of example, and not by way of limitation, in the figures of the accompanying drawings.

DETAILED DESCRIPTION

Embodiments of a method and system for positioning a patient for radiation treatment are described herein. In one embodiment, projection images of a patient positioned on a treatment couch are obtained. One of the projection images is displayed with a corresponding synthetic projection image on a display. The position of the projection image on the display is adjusted to approximately align with the corresponding synthetic projection image in response to a user dragging the projection image on the display with a user interface device. The treatment couch is then moved to position the patient based on position adjustments of the projection image.

Embodiments of the present invention may allow a patient to be efficiently positioned in relation to an imaging center of the radiation treatment system. Furthermore, embodiments of the present invention position the patient without requiring a user to understand the geometry behind translating the on-screen movement of projection images into movement of a treatment couch and a patient in three dimensions.

Figure 1:
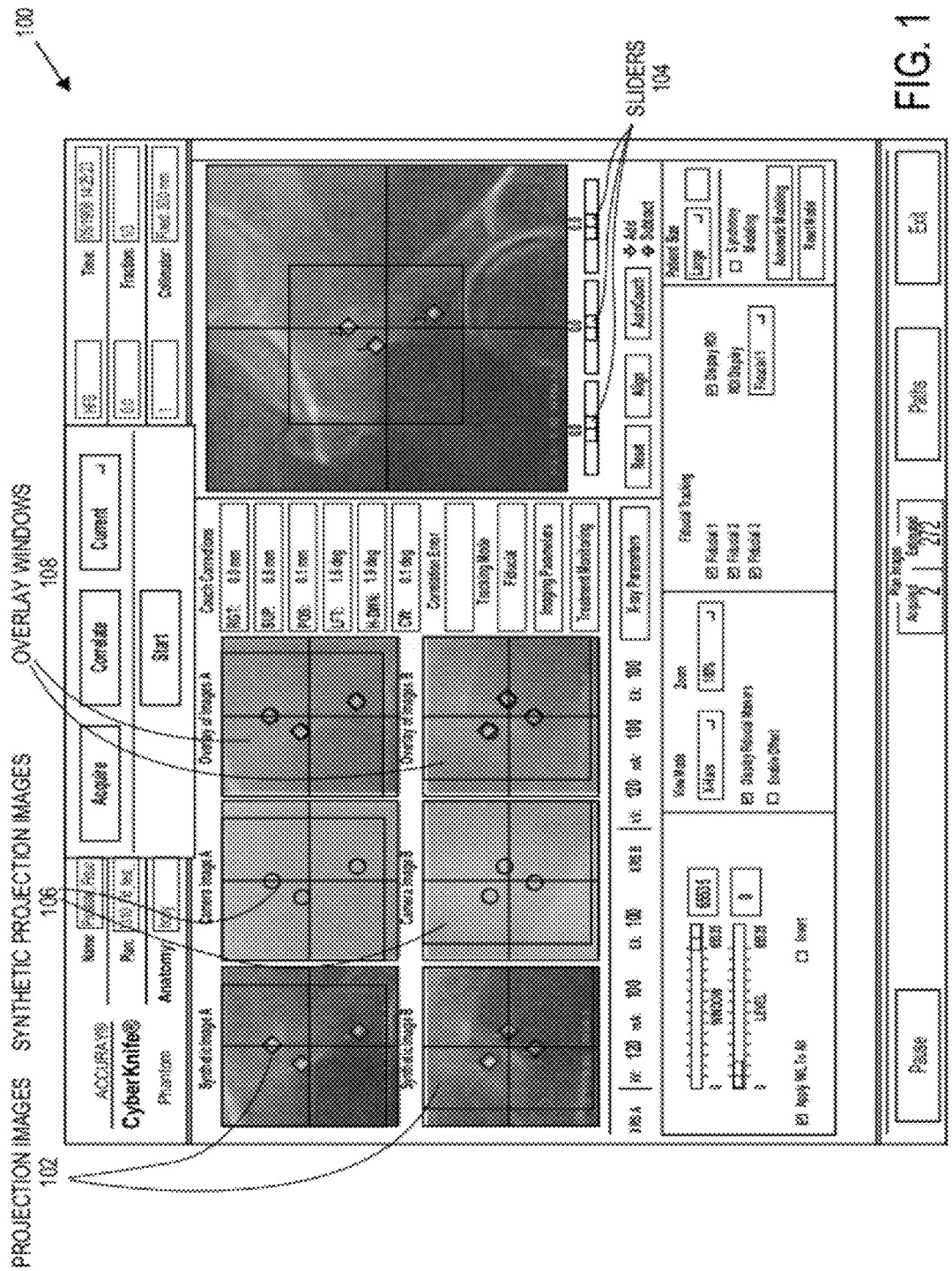
FIG. 1 illustrates a current user interface for adjusting the position of at least one projection image.
Figure 2:
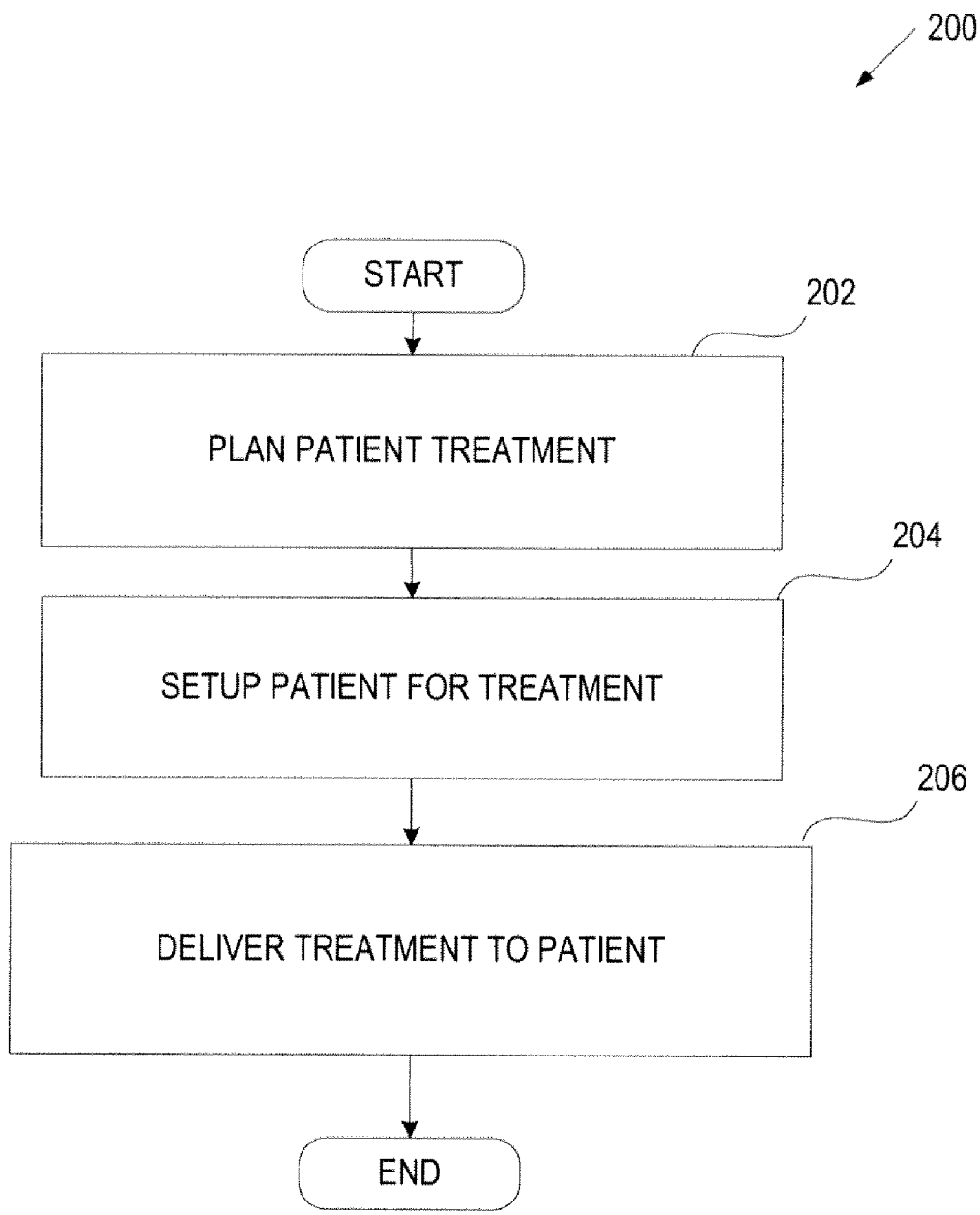
FIG. 2 is a flow diagram of one embodiment of a workflow for patient treatment.

FIG. 2 is a flow diagram of one embodiment of a workflow 200 for patient treatment. It should be noted that one or more of the stages described in relation to FIG. 2 may not necessarily be required for embodiments of the present invention, but are described in order to provide a better context for the discussion of certain embodiments of the present invention. Moreover, one or more steps illustrated and discussed as being within a particular stage, may be performed outside of that stage. It should also be noted that although embodiments describe herein refer to use with radiation treatment, the embodiments described herein may also be used in other applications. The workflow 200 of FIG. 2 may also be discussed at times in reference to the treatment systems of FIG. 8 and the treatment delivery system 4000 of FIG. 4.

Figure 8:
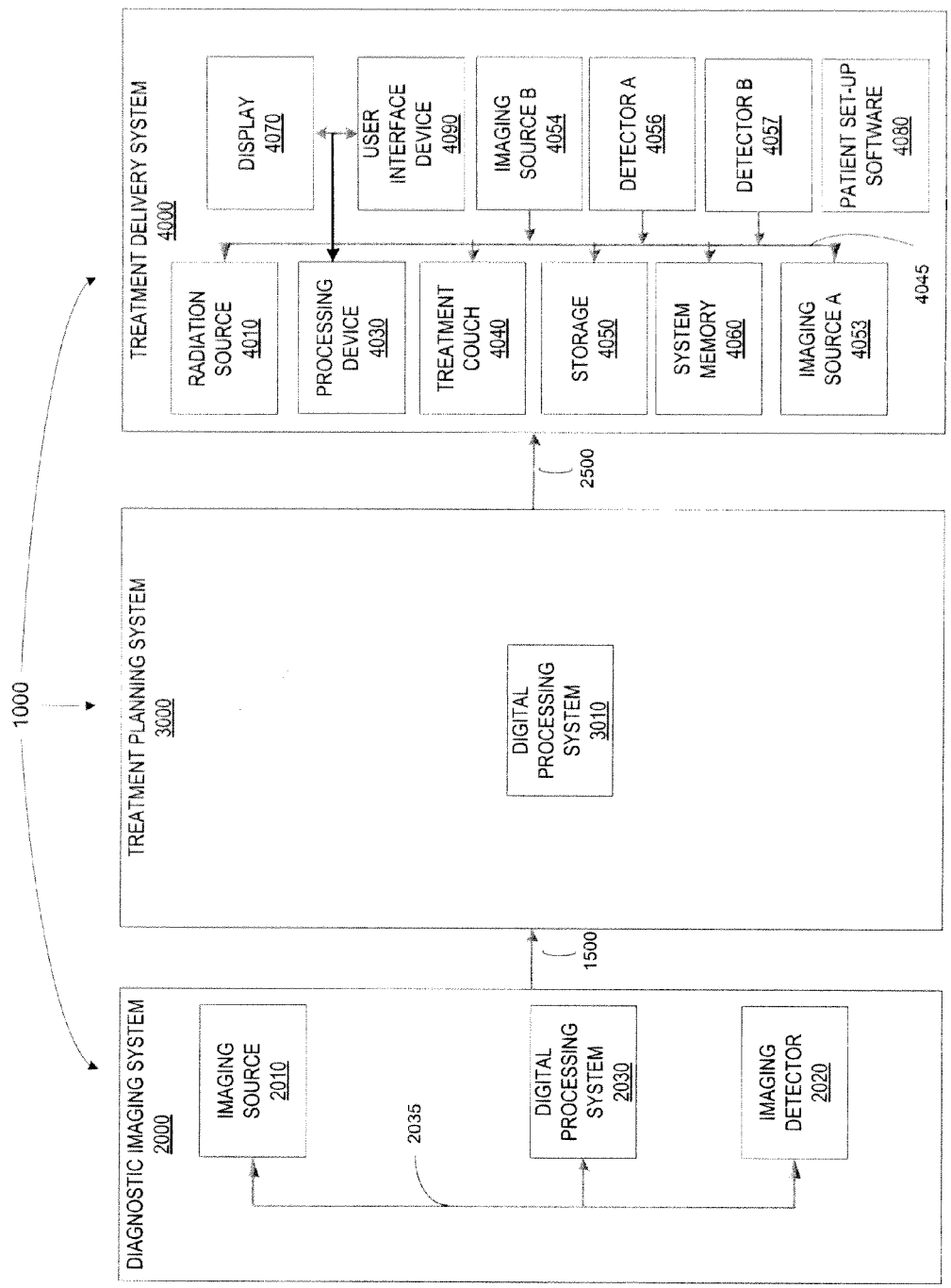
FIG. 8 illustrates one embodiment of systems that may be used to perform radiation treatment in which features of the present invention may be implemented.

In the workflow 200 illustrated in FIG. 2, the patient radiation therapy includes a treatment planning stage 202, a patient setup stage 204, and a treatment delivery stage 206. Treatment planning system 3000 of FIG. 8 is used to plan patient treatment at stage 202. As part of planning the patient treatment, the treatment planning system 3000 may identify a prescribed radiation dose for a patient and create a treatment plan for the patient based on pre-treatment images taken of the patient. In some embodiments, the pre-treatment images may be obtained using a computed tomography (CT) scanner. In order to create a CT scan, an X-ray source produces a fan beam of X-rays that travels through the patient and impinges on a detector. While the treatment table is stationary, a cross-sectional image of the patient is obtained by rotating the X-ray source and detector around the patient and scanning a transverse slice of the body from different angular positions.

After each cross-sectional slice is complete, the table is advanced and the next cross-sectional slice is obtained. A three-dimensional (3-D) image (CT volume) is obtained by integrating the image data from the slices. The CT scan is used to develop a treatment plan that calculates the angle, duration and intensity of X-ray beams needed to deliver the prescribed radiation dose.

The treatment planning system 3000 also generates synthetic projection images of the patient as part of the treatment planning process 202. In some embodiments, the synthetic projection images are digitally reconstructed radiograms (DRRs), rendered from the pre-treatment CT scan. A DRR is a synthetic X-ray image produced by combining data from the CT scan slices and computing a two-dimensional (2-D) projection through the slices that approximates the geometry of a real-time imaging system.

Once a treatment plan 202 is developed, the next stage of the workflow 200 is to position the patient, using the treatment couch 4040, within the treatment delivery system 4000 of FIG. 8 for delivery of radiation treatment. In order to implement the treatment plan 202, the patient on treatment couch 4040 must be properly positioned (set-up) within the treatment delivery system 4000. At stage 204, patient set-up software 4080 is used to set up the patient for treatment. As part of setting up the patient for treatment, the patient set-up software 4080 determines a proper alignment for the patient in relation to an imaging center of the treatment delivery system 4000. In some embodiments, the treatment delivery system 4000 is used to obtain one or more projection images of the patient and the patient set-up software determines position adjustments for the treatment couch (and, thereby, the patient) based on the obtained images.

Figure 4:
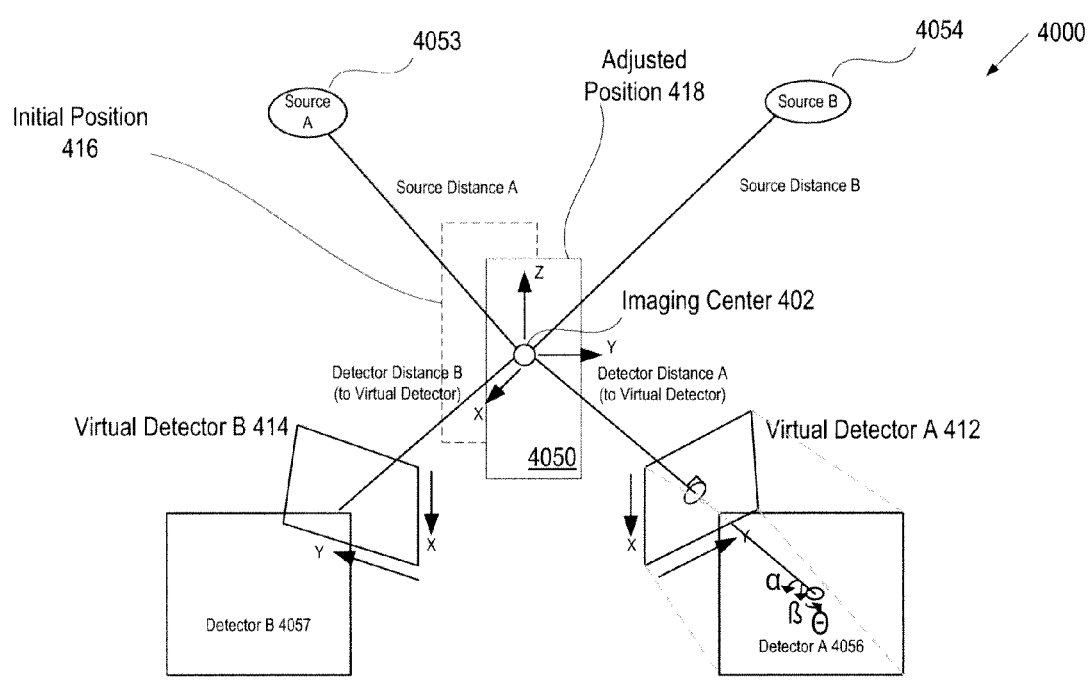
FIG. 4 illustrates an embodiment of a treatment delivery system.

In some embodiments, the projection images are generated from X-ray images, the acquisition of which is illustrated in FIG. 4. Treatment delivery system 4000 of FIG. 4 includes a treatment couch 4040 on which a patient is positioned, image source A 4053 aimed at corresponding detector A 4056, and image source B 4054 aimed at corresponding detector B 4057. Image source A 4053 and image source B 4054 may project X-ray imaging beams through a target area of a patient and to the corresponding detectors 4056 and 4057 to create a pair of stereoscopic X-ray images. The stereoscopic pair of X-ray images is then used to create a pair of projection images. Alternatively, the projection images may be obtained by using a cone beam CT scanner (not shown) that produces a set of projected 2-D X-ray images by rotating one or more pairs of X-ray sources and detectors around a patient. In another embodiment, the projection images may be generated from fluoroscopy images created using a fluoroscope.

The mechanisms for adjustment of a treatment couch are known in the art; accordingly, a detailed discussion is not provided herein. As part of the adjustment, an algorithm may be used that calculates the proper couch position based on the acquired image. If the algorithm is only capable of making fine adjustments to the position of the patient, the initial position of the treatment couch 4040 may be outside the set of initial states for which the algorithm can return a useful result (e.g., the algorithm is unable to return any result, the algorithm outputs a result with a low confidence level, etc). In such a case, the patient set-up software 4080 determines a position adjustment for the treatment couch 4040 based on a user dragging one or more displayed projection images in relation to a displayed synthetic projection image with a user interface device. In one embodiment, the synthetic projection image is a DRR acquired during the treatment planning stage 202. After the treatment couch 4040 is moved, another image is acquired and the patient set-up software 4080 determines whether the patient is ready to treat (in which case the workflow moves to stage 206), whether the patient can now be aligned using the algorithm, or whether the user will once again have to reposition the projection images. Patient alignment will be described in more detail below in conjunction with FIGS. 3, 4 and 5.

After treatment planning and patient set-up are completed, the treatment delivery system 4000 delivers treatment to the patient at stage 206. As part of treatment delivery, the treatment delivery system 4000 delivers the prescribed radiation dose to a target region on the patient according to the treatment plan developed during the treatment planning stage 202.

Figure 3:
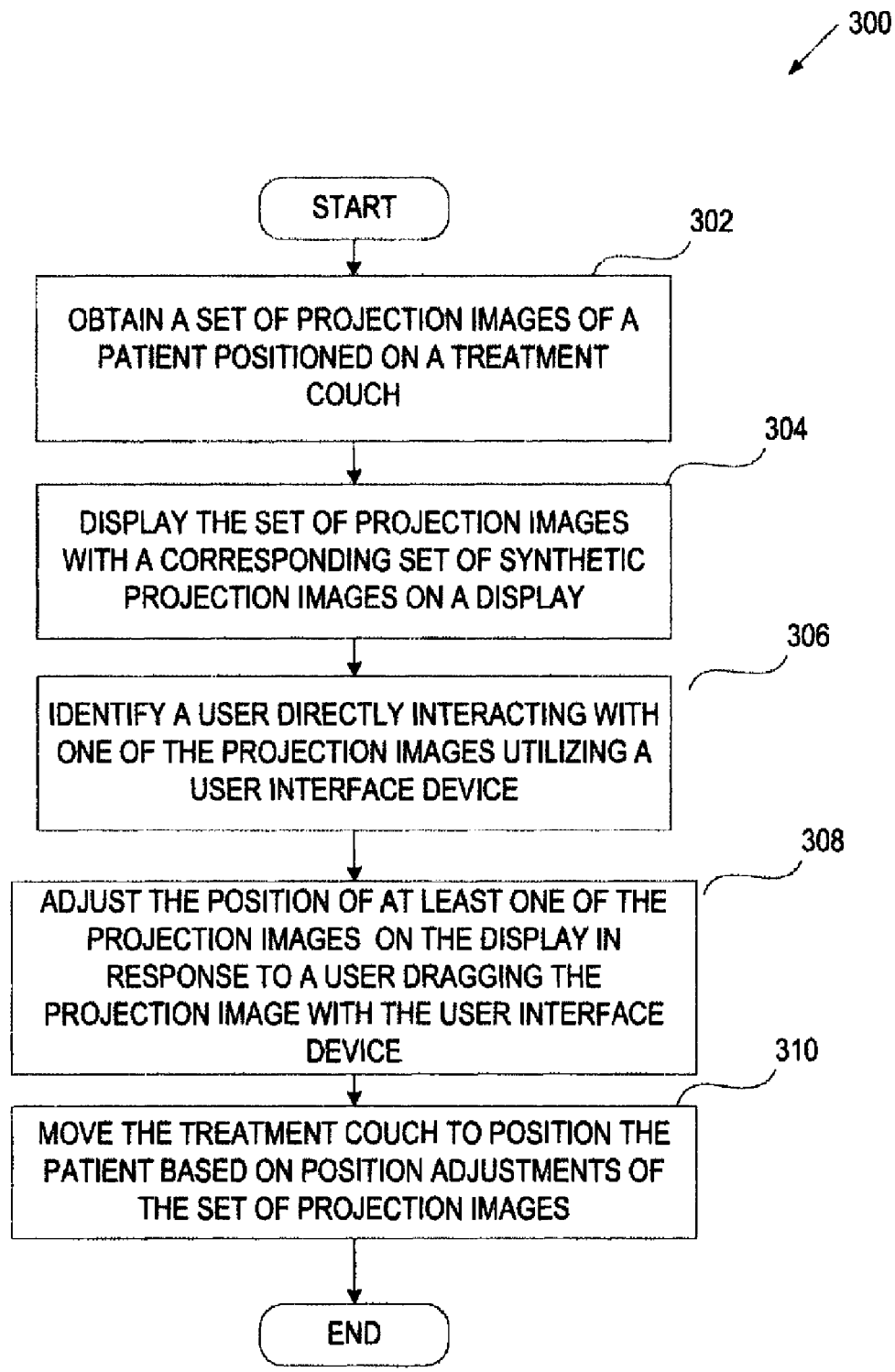
FIG. 3 is a flow diagram of one embodiment of a method for positioning a patient.

FIG. 3 is a flow diagram of one embodiment of a method 300 for positioning a patient. In this embodiment, the patient set-up software 4080 obtains a set of projection images of a user positioned on a treatment couch 4040. The projection images may be generated from X-ray images taken by a treatment delivery system such as treatment delivery system 4000 of FIG. 4.

In one embodiment, the patient set-up software 4080 displays the set of projection images (obtained using treatment delivery system 4000, a cone beam CT scanner, or a fluoroscope as described above in conjunction with FIG. 2) with a corresponding set of synthetic projection images on a display in step 304. The synthetic projection images may be DRRs obtained during a treatment planning stage as described in conjunction with step 202 of FIG. 2. In one embodiment, the patient set-up software 4080 displays each projection image separately in one portion of the display as well as displaying each projection image alongside a corresponding synthetic projection image in a second portion of the display.

At step 306, the patient set-up software 4080 identifies that a user has directly interacted with one of the projection images on the display utilizing a user interface device. The user interface device may be a mouse having a cursor used to interact with the projection image, an electronic pen used to directly contact the projection image, etc.

The patient set-up software 4080 adjusts the position of the projection image on the display in response to the user dragging the projection image with the user interface device at step 308. When the user drags the projection image, the patient set-up software 4080 may also adjust the position of another projection image because of the geometrical dependency between the two images. For example, in the case where the inferior/superior axis is dependent between the projection images, when the user drags a first projection image along the inferior/superior axis, the patient set-up software 4080 moves the second projection image the opposite direction along the same axis. The dependency between projection images will be described in more detail in conjunction with FIG. 7.

At step 310, treatment delivery system 4000 moves the treatment couch to position the patient based on position adjustments determined by patient set-up software 4080. The patient set-up software 4080 may calculate the position adjustments after receiving an input from the user that each projection image has been moved to grossly align with the corresponding synthetic projection image. A projection image and a corresponding synthetic projection image are aligned when a structure visible in the projection image has been aligned to overlay a corresponding structure in the synthetic projection image. The structure can be a skeletal structure, a fiducial or other marker, a tumor, etc. In some cases, more than one structure may be visible in a projection image. When the structure(s) in the projection image overlays the same structure(s) in the projection image, the user indicates that the couch is ready to be moved and the patient set-up software 4080 determines a proper position adjustment for the treatment couch 4040 based on the user adjustments of the projection images. Alternatively, the patient set-up software 4080 may detect when each projection image is aligned with the corresponding synthetic projection image and instruct the treatment delivery system 4000 to move the couch without user input.

In order to move the treatment couch to better align the patient, the patient set-up software 4080 computes a back projection on the projection images onto a three dimensional space. After the projection is computed, the treatment delivery system 4000 positions the patient in approximate alignment with an imaging center of a treatment delivery system based on the back projection. Computing the back projection will discussed in more detail below in conjunction with FIG. 4.

Referring to FIG. 4, treatment delivery system 4000 contains an image source A 4053 aimed at corresponding detector A 4056, and an image source B 4054 aimed at corresponding detector B 4057. Imaging center 402 is a three-dimensional point defined to be the center of the imaging coordinate system. Thus, the location of imaging center 402 is (0, 0, 0) in the (x, y, z) coordinate system. The distance from image source A 4053 to imaging center 402 is defined as source distance A, and the distance from image source B 4054 to the imaging center is defined as source distance B. Similarly, the distance from virtual detector A 412 to imaging center 402 is defined as detector distance A, and the distance from virtual detector B 414 to the imaging center is defined as detector distance B.

Virtual detector A 412 and Virtual detector B 414 may be a representation of the projection images generated from actual detectors 4056 and 4057, processed for ease of consumption by the user. Embodiments of the present invention can operate without the presence of virtual detector A 412 and virtual detector B 414, which are described here for ease of understanding. The angles $\alpha$, $\beta$, and $\Theta$ describe the difference in angular orientation between the actual and virtual detectors.

A separate two dimensional coordinate system centered in the middle of the virtual detector is defined for each virtual detector. When a user requests a couch position by dragging the projection images to overlay their corresponding synthetic projection images, the position of each projection image is specified in the two-dimensional coordinate system of the corresponding virtual detector (for example, the position of a projection image generated from an image taken by image source A is specified in the two-dimensional coordinate system of virtual detector A). The new location of a treatment couch is then calculated based on the position of the projection images. In one embodiment, this is done by using the distances and angles specified in FIG. 4 to define a transformation from the two-dimensional detector coordinate systems to the three-dimensional imaging coordinate system. After the new location of the treatment couch is calculated, treatment delivery system 4000 moves the treatment couch 4040—(for example, from an initial position 416 to an adjusted position 418) relative to the imaging center 402.

In one example, the image sources and the detectors are in the same plane and source distance A=source distance B=$N_1$, detector distance A=detector distance B=$N_2$, $\alpha$=45 degrees, $\beta$=90 degrees, and $\theta$=0 degrees. In this case, when the user has positioned the first projection image at coordinates ($x_A$, $y_A$) and the second projection image at coordinates ($x_B$, $y_B$), the desired new imaging point ($X_i$, $Y_i$, $Z_i$) (e.g., the desired position of the treatment couch) may be computed by deriving $TRANS_Y$ and $TRANS_Z$ (Equations 1 and 2) and using those to compute $X_i$, $Y_i$, and $Z_i$ (Equations 3, 4, and 5).

$$TRANS_Y = N_1 * y_A * (N_2 - y_B)/((N_1+N_2)^2 - (y_A * y_B)) \quad \text{(Eq. 1)}$$

$$TRANS_Z = y_B * (N_1 - TRANS_Y)/(N_1+N_2) \quad \text{(Eq. 2)}$$

$$X_i = 0.5 * (x_A * (N_1 - TRANS_Z)/(N_1+N_2)) + (x_B * (N_1 - TRANS_Y)/(N_1+N_2)) \quad \text{(Eq. 3)}$$

$$Y_i = (TRANS_Y - TRANS_Z)/SQRT(2) \quad \text{(Eq. 4)}$$

$$Z_i = (TRANS_Y + TRANS_Z)/SQRT(2) \quad \text{(Eq. 5)}$$

Figure 5:
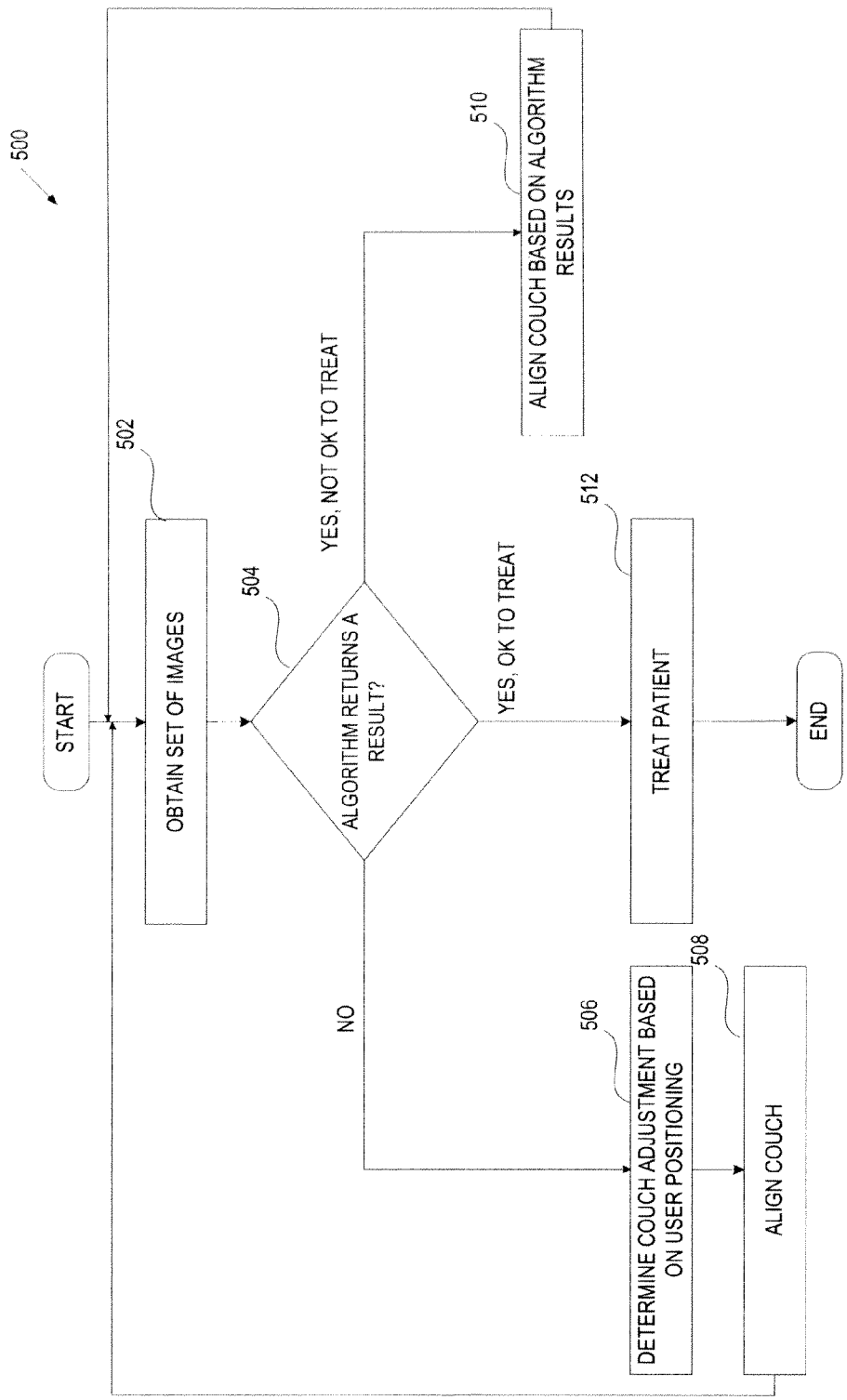
FIG. 5 is a flow diagram of one embodiment of a method for positioning a patient.

FIG. 5 is a flow diagram of one exemplary embodiment of a method 500 for patient treatment. Referring to FIG. 5, patient set-up software 4080 obtains a set of projection images at step 502. The projection images may be generated from X-ray images taken by treatment delivery system 4000 of FIG. 4.

At step 504, the patient set-up software 4080 checks to see if a treatment couch alignment algorithm has returned a result. In some cases, the algorithm may not be able to return a result because the patient is too far out of alignment with the imaging center for the algorithm to calculate the necessary adjustment. In these cases, the method moves on to step 506. If the algorithm returns a result, but the treatment couch 4040 still requires alignment before the patient can be treated, the method moves on to step 510. If the algorithm returns that the patient is properly aligned and is ready to be treated, the algorithm moves on to step 512, where the treatment delivery system 4000 begins treatment of the patient. The method then ends.

At step 506, if the algorithm has not returned a result, the patient set-up software 4080 determines a couch adjustment based on user positioning of the projection images on a display. The patient set-up software 4080 may determine the couch adjustment as described in method 300 of FIG. 3 and in conjunction with FIG. 4. At step 508, the treatment delivery system 4000 moves the treatment couch 4040 to align the patient in accordance with the couch adjustments determined by the patient set-up software 4080. The method then returns to step 502. Because the user is able to cause the proper couch movement without having to be aware of the geometry involved in transforming the movement of the projection images into three dimensions, the number of times that the user has to position the images and the number of images that need to be obtained (at step 502) before the algorithm returns a useful result are minimized.

If the algorithm has returned a result indicating that the couch still requires alignment before the patient can be treated, treatment delivery system 4000 moves the couch based on the algorithm results at step 510. The method then returns to step 502.

Figure 6A:
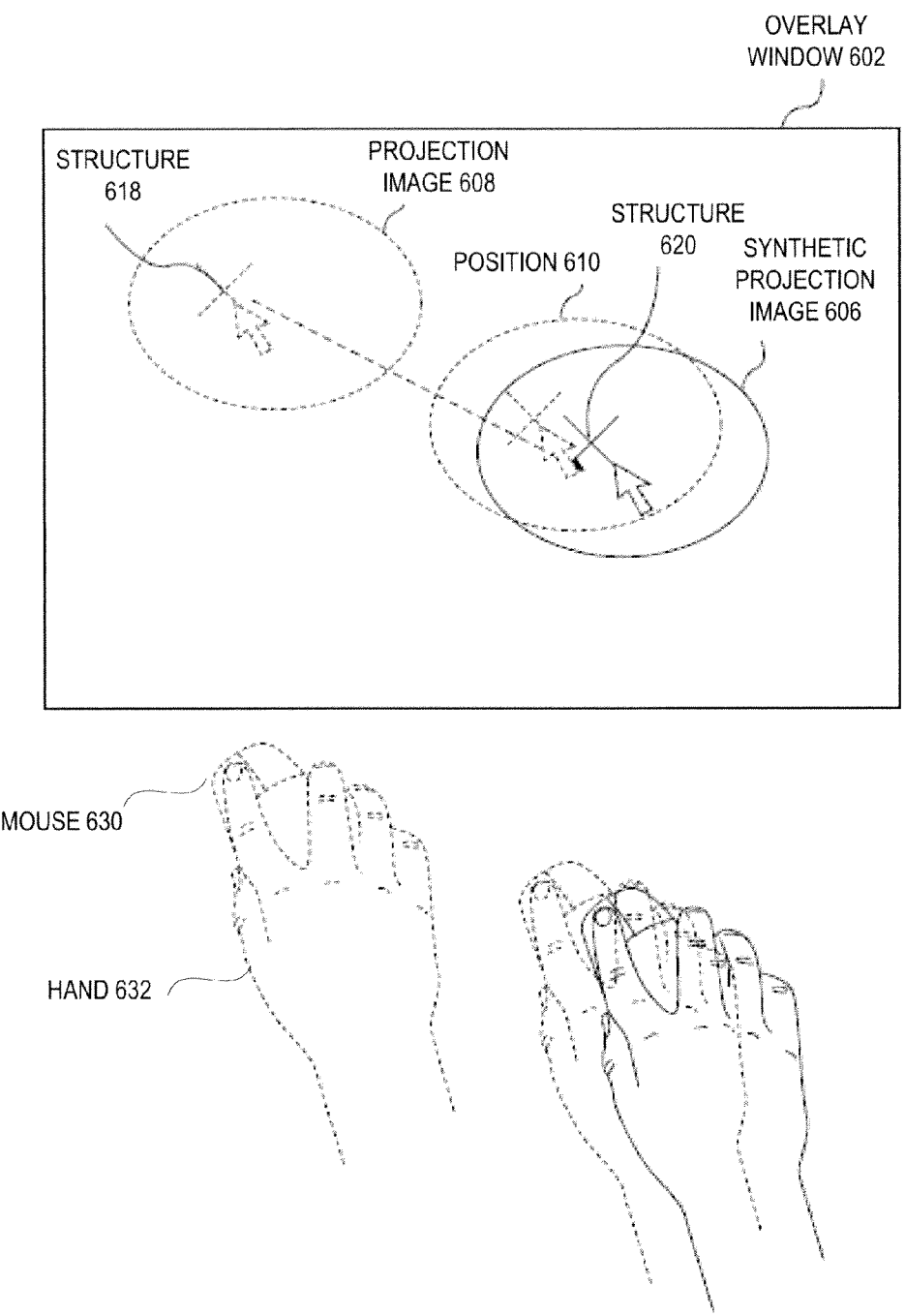
FIG. 6A illustrates the operation of an embodiment of adjusting the position of a projection image with a user interface device.

FIG. 6A illustrates the operation of one embodiment of adjusting the position of a projection image with a user interface device. In FIG. 6A, overlay window 602 displays a projection image 608 along with a synthetic projection image 606. The position of the synthetic projection image 606 is fixed, while a user can adjust the position of the projection image 608 with a user interface device. In this embodiment, the user interface device is a mouse 630. The synthetic projection image contains a visible structure 620. The same structure 618 is visible in the projection image. The structure may be a skeletal structure, a fiducial or other marker, a tumor, or any other structure that is visible in both images.

The user (i.e., with their hand 636) selects the visible structure 618 of projection image 608 at its initial position with a cursor controlled by the mouse 630. The user then moves the mouse 630 while the projection image 608 is selected and drags the structure (and, therefore, the projection image) to position 610. The user continues to drag the projection image 608 with the mouse-controlled cursor until the projection image overlays the synthetic projection image 606. The user may identify that the projection image overlays the synthetic projection image 606 and no further movement is necessary when the visible structures in each image are in the same position in the overlay window 602. When no more movement is necessary (e.g., when all displayed projection images overlap their corresponding synthetic projection images), the user may make a selection (not shown) that initiates a movement of a treatment couch based on the changes in the position of the projection image. In alternative embodiments, other types of user interface devices may be used such as an electronic pen as discussed below in relation to FIG. 6B.

Figure 6B:
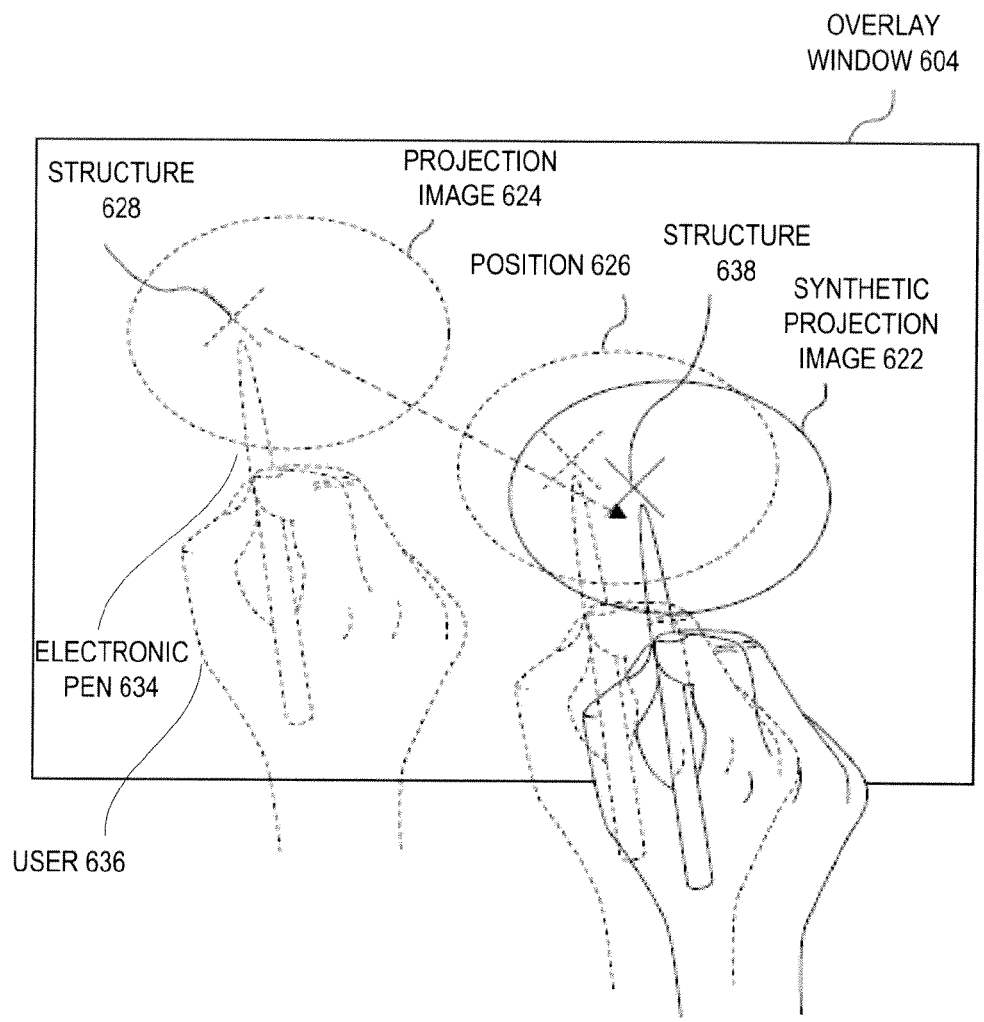
FIG. 6B illustrates the operation of another embodiment of adjusting the position of a projection image with a user interface device.

FIG. 6B illustrates the operation of adjusting the position of a projection image with a user interface device according to another embodiment. In this embodiment, the user interface device is an electronic pen 634. At node 618, a user 636 selects a visible structure 628 in the projection image 624 at its initial position in overlay window 604 with the electronic pen 634. The user 636 then moves the pen 634 along the overlay window 604 while the structure 628 is selected and drags the projection image 624 to position 610. The user continues to drag the visible structure 628 (and, therefore, the projection image 624) with the electronic pen until structure 628 of in the projection image 624 is in the same position as visible structure 638 in synthetic projection image 606 (i.e., until projection image 624 overlays the synthetic projection image 606).

Figure 7:
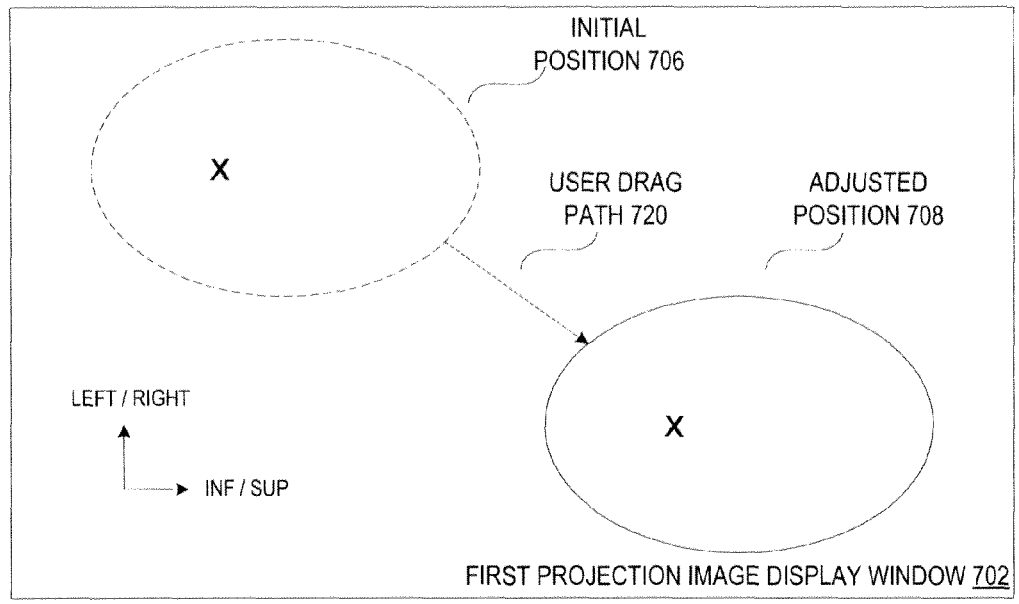
FIG. 7 illustrates the dependency between projection images according to some embodiments of the present invention.
Figure 7:
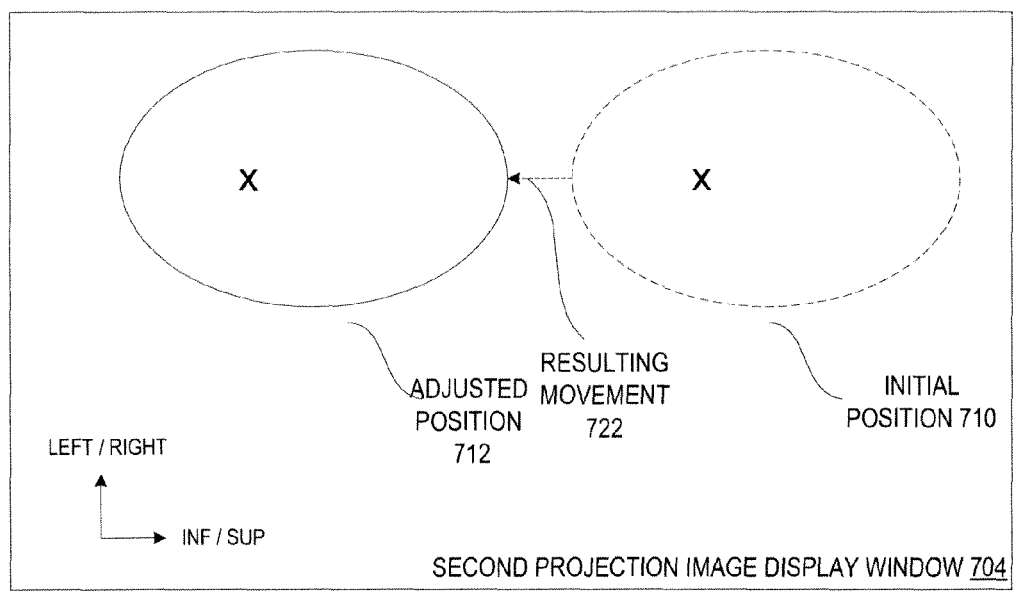

FIG. 7 illustrates the dependency between projection images according to some embodiments of the present invention. In FIG. 7, a first projection image is initially displayed at position 706 in a first projection image display window 702. A second projection image is initially displayed at position 710 in a second projection image display window 704. Corresponding synthetic projection images may also be displayed in the projection image display windows 702 and 704. Alternatively, the synthetic projection images may be displayed in their own display windows. A user may adjust the position of either displayed projection image along the horizontal and/or vertical axis by dragging the image with a user interface device (e.g., a mouse or an electronic pen). Because moving the projection images simulates movement of a treatment couch in three dimensions in order to align a patient to an imaging center, the horizontal and vertical axes are not necessarily relative to anatomical coordinates of the human body. A movement along the horizontal axis moves the projection image along the inferior/superior axis of the patient, and a movement along the vertical axis moves the image along a combination of the left/right and ant/post axes of the patient.

In the example geometry described above in conjunction with FIG. 4 (wherein the image sources and the detectors are in the same plane and source distance A=source distance B=$N_1$, detector distance A=detector distance B=$N_2$, $\alpha$=45 degrees, $\beta$=90 degrees, and $\theta$=0 degrees), when a user drags the first projection image along a path 720 to an adjusted position 708, the second projection image has a resulting movement 722 to an adjusted position 712. Because the displayed images are projections of a stereoscopic (three-dimensional) pair of images, the left/right and ant/post axes are independent between the displayed images while moving one projection image along the inferior/superior axis results in a corresponding movement of the other projection image (the inferior/superior axis is shared between the two projection images). Due to this dependency between the displayed projection images, the resulting movement 722 of the second projection image is only along the inferior/superior axis and, in some embodiments, is equal in magnitude and opposite in direction to the inferior/superior component of the drag path 720 of the first projection image. In geometries that differ from the example described above, other relationships between the projection images may apply.

FIG. 8 illustrates one embodiment of systems that may be used to perform radiation treatment in which features of the present invention may be implemented. Systems 1000 may include a diagnostic imaging system 2000, a treatment planning system 3000, and a treatment delivery system 4000.

Diagnostic imaging system 2000 may be any system capable of producing medical diagnostic images of a volume of interest (VOI) in a patient that may be used for subsequent medical diagnosis, treatment planning and/or treatment delivery. For example, diagnostic imaging system 2000 may be a CT system, a magnetic resonance imaging (MRI) system, a positron emission tomography (PET) system, an ultrasound (US) system or the like. For ease of discussion, diagnostic imaging system 2000 may be discussed below at times in relation to a CT x-ray imaging modality. However, other imaging modalities such as those above may also be used.

Diagnostic imaging system 2000 includes an imaging source 2010 to generate an imaging beam (e.g., x-rays, ultrasonic waves, radio frequency waves, etc.) and an imaging detector 2020 to detect and receive the beam generated by imaging source 2010, or a secondary beam or emission stimulated by the beam from the imaging source (e.g., in an MRI or PET scan). In one embodiment, diagnostic imaging system 2000 includes two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s), which may be diametrically opposed to the x-ray sources. A single large imaging detector, or multiple imaging detectors, may also be used that would be illuminated by each x-ray imaging source. As would be appreciated by one of ordinary skill in the art, other numbers and configurations of imaging sources and imaging detectors may be used.

The imaging source 2010 and the imaging detector 2020 are coupled to a digital processing system 2030 to control the imaging operation and process image data. Diagnostic imaging system 2000 includes a bus or other means 2035 for transferring data and commands among digital processing system 2030, imaging source 2010 and imaging detector 2020. Digital processing system 2030 may include one or more general-purpose processors (e.g., a microprocessor), special purpose processor such as a digital signal processor (DSP), or other types of processing devices, such as a controller, field programmable gate array (FPGA), or the like. Digital processing system 2030 may also include other components (not shown) such as memory, storage devices, network adapters and the like. Digital processing system 2030 may be configured to generate digital diagnostic images in a standard format, such as the DICOM format, for example. In other embodiments, digital processing system 2030 may generate other standard or non-standard digital image formats. Digital processing system 2030 may transmit diagnostic image files (e.g., the aforementioned DICOM formatted files) to treatment planning system 3000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 3000 includes a digital processing system 3010 to receive and process image data. Digital processing system 3010 may include one or more general-purpose processors (e.g., a microprocessor), special purpose processor such as a digital signal processor (DSP), or other types of processing devices, such as a controller, field programmable gate array (FPGA), or the like. Digital processing system 3010 may also include other components (not shown) such as memory, storage devices, network adapters and the like.

It will be appreciated that treatment planning system 3000 represents only one example of a treatment planning system, which may have many different configurations and architectures, which may include more components or fewer components than treatment planning system 3000 and which may be employed with the present invention. The treatment planning system 3000 may also include MIRIT (Medical Image Review and Import Tool) to support DICOM imports (so images can be fused and targets delineated on different systems and then imported into the treatment planning system for planning and dose calculations), expanded image fusion capabilities that allow the user to treatment plan and view dose distributions on any one of the various imaging modalities (e.g., MRI, CT, PET, etc.). Additional details of the treatment planning systems would be appreciated by one of ordinary skill in the art; accordingly, a more detailed discussion is not provided.

Treatment planning system 3000 may be linked to treatment delivery system 4000 via a data link 2500, which may be a direct link, a LAN link or a WAN link as discussed above with respect to data link 1500. It should be noted that when data links 1500 and 2500 are implemented as LAN or WAN connections, any of diagnostic imaging system 2000, treatment planning system 3000 and/or treatment delivery system 4000 may be in decentralized locations such that the systems may be physically remote from each other. Alternatively, any of diagnostic imaging system 2000, treatment planning system 3000 and/or treatment delivery system 4000 may be integrated with each other in one or more systems.

Treatment delivery system 4000 includes a therapeutic and/or surgical radiation source 4010 to administer a prescribed radiation dose to a target volume in conformance with a treatment plan. Treatment delivery system 4000 may also include an imaging source A 4053, an imaging source B 4054, a detector A 4056, and a detector B 4057 to capture intra-treatment images of a patient volume (including the target volume) for registration or correlation with the diagnostic images described above in order to position the patient with respect to the radiation source.

Treatment delivery system 4000 may also include a processing device 4030 to control radiation source 4010, imaging source A 4053, imaging source B 4054, detector A 4056, detector B 4057, and a patient support device such as a treatment couch 4040. Processing device 4030 may represent one or more general-purpose processors (e.g., a microprocessor), special purpose processor such as a DSP, or other types of processing devices, such as a controller, FPGA, or the like. Processing device 4030 may be configured to execute instructions for patient set-up software 4080 discussed herein. In one embodiment, the instructions include receiving projection images of a patient positioned on a treatment couch, displaying a projection image with a corresponding synthetic projection image on a display, adjusting the position of the projection image on the display in response to a user dragging the projection image on the display with a user interface device, and transmitting treatment couching positioning data based on position adjustments of the projection image.

Treatment delivery system 4000 may also include system memory 4060 that may include a random access memory (RAM), or other dynamic storage devices, coupled to processing device 4030 by bus 4045, for storing information and instructions to be executed by processing device 4030. System memory 4060 also may be used for storing temporary variables or other intermediate information during execution of instructions by processing device 4010. System memory 4060 may also include a read only memory (ROM) and/or other static storage devices coupled to bus 4045 for storing static information and instructions for processing device 4030. In one embodiment, the system memory 4060 is a machine-readable storage medium having stored thereon instructions, which when executed by the processing device, perform the operations described herein regarding sequential optimization.

Treatment delivery system 4000 may also include storage device 4050, representing one or more storage devices (e.g., a magnetic disk drive or optical disk drive) coupled to bus 4045 for storing information and instructions. Storage device 4050 may be used for storing instructions for performing the treatment planning steps discussed herein, such as the image alignment algorithms. Treatment delivery system 4000 may share its database (e.g., data stored in storage device 4050) with a treatment planning system, such as treatment planning system 3000, so that it may not be necessary to export from the treatment planning system prior to treatment delivery.

Processing device 4030 may also be coupled to a display device 4070, such as a cathode ray tube (CRT) or liquid crystal display (LCD), for displaying information (e.g., a two-dimensional or three-dimensional representation of the VOI) to the user. A user interface device 4090, such as a keyboard, may be coupled to processing device 4030 for communicating information and/or command selections to processing device 4030. One or more other user interface devices (e.g., a mouse 730, electronic pen 734, a trackball or cursor direction keys) may also be used to communicate directional information, to select commands for processing device 4030 and to control cursor movements on display 4070.

It will be appreciated that treatment delivery system 4000 represents only one example of a treatment planning system, which may have many different configurations and architectures, which may include more components or fewer components than treatment delivery system 4000 and which may be employed with the present invention. For example, some systems often have multiple buses, such as a peripheral bus, a dedicated cache bus, etc.

Processing device 4030 may be coupled to radiation source 4010, imaging source A 4053, imaging source B 4054, detector A 4056, detector B 4057 and treatment couch 4040 by a bus 4045 or other type of control and communication interface.

Figure 9:
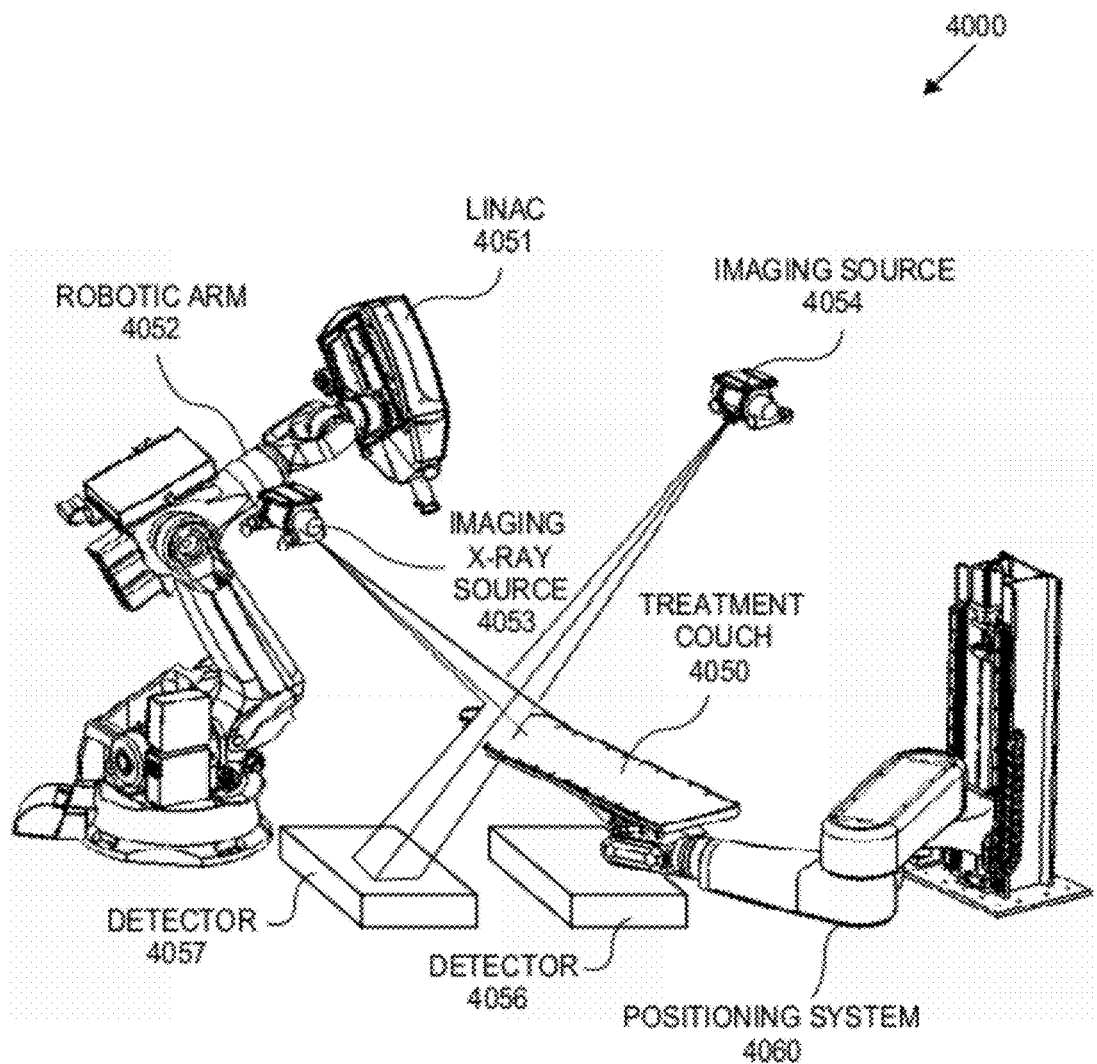
FIG. 9 illustrates another embodiment of a treatment delivery system.

In one embodiment, as illustrated in FIG. 9, treatment delivery system 4000 may be an image-guided, robotic-based radiation treatment system (e.g., for performing radiosurgery) such as the CyberKnife® system, developed by Accuray Inc. of California. In FIG. 10, the radiation source 4010 is represented by a linear accelerator (LINAC) 4051 mounted on the end of a robotic arm 4052 having multiple (e.g., 5 or more) degrees of freedom in order to position the LINAC 4051 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered either in a single session (mono-fraction) or in a small number of sessions as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment-planning phase.

In FIG. 9, an imaging system is represented by X-ray sources 4053 and 4054 and X-ray image detectors (imagers) 4056 and 4057. In one embodiment, for example, two x-ray sources 4053 and 4054 may be nominally aligned to project imaging x-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each x-ray imaging source. As would be appreciated by one of ordinary skill in the art, other numbers and configurations of imaging sources and imagers may be used.

Processing device 4030 may implement algorithms to register images obtained from imaging source A 4053, imaging source B 4054, detector A 4056, and detector B 4057 with pre-operative treatment planning images in order to align the patient on the treatment couch 4050 within the treatment delivery system 4000, and to position the radiation source with respect to the target volume.

The treatment couch 4050 may be coupled to another robotic arm of a positioning system 4060 having multiple (e.g., 5 or more) degrees of freedom, such as the ROBOCOUCH® treatment couch, developed by Accuray Incorporated. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the AXUM® treatment couch developed by Accuray Incorporated of California, or other types of treatment tables as would be appreciated by one of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met. In one particular embodiment, the gantry based system may have an O-ring with a LINAC mounted on a gimbaled head assembly.

In other embodiments, yet another type of treatment delivery system 4000 may be used, for example, a stereotactic frame system such as the GAMMAKNIFE®, available from Elekta of Sweden. With such a system, the optimization algorithm (also referred to as a sphere packing algorithm) of the treatment plan determines the selection and dose weighting assigned to a group of beams forming isocenters in order to best meet provided dose constraints.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry), and seismic surveying. In such applications, for example, "treatment" may refer generally to the application of radiation beam(s).

Embodiments of the present invention include various steps, as described herein. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software.

Embodiments of the present invention may be provided as a computer program product, or software, which may include a machine-readable storage medium having stored thereon instructions, which may be used to program a computer system (or other electronic devices) to perform a method of the operations described herein. A machine-readable medium includes any mechanism for storing or transmitting information in a form (e.g., software, processing application) readable by a machine (e.g., a computer). The machine-readable storage medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM), flash memory, or other types of medium suitable for storing electronic instructions. The machine-readable transmission medium may include, but is not limited to, electrical, optical, acoustical, or other type of medium suitable for transmitting electronic instructions.

Embodiments of the present invention may also be practiced in distributed computing environments where the machine-readable storage medium is stored on and/or executed by more than one computer system. In addition, the information transferred between computer systems may either be pulled or pushed across the communication medium connecting the computer systems, such as in a remote diagnosis or monitoring system. In remote diagnosis or monitoring, a user may utilize embodiments of the present invention to diagnose or monitor a patient despite the existence of a physical separation between the user and the patient. In addition, the treatment delivery system may be remote from the treatment planning system.

In the foregoing specification, the treatment planning, patient set-up, and treatment delivery software may be executed by processing logic that may comprise hardware (processing device, circuitry, dedicated logic, etc.), software (such as is run on a general purpose computer system or a dedicated machine), firmware (such as embedded software), or any combination thereof.

In the foregoing specification, the invention has been described with reference to specific exemplary embodiments thereof. It will be evident, however, that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A computer-implemented method comprising:
   obtaining a plurality of projection images of a patient positioned on a treatment couch;
   displaying at least one of the plurality of projection images with a corresponding synthetic projection image on a display;
   adjusting the position of the at least one projection image on the display to approximately align with the corresponding synthetic projection image in response to a user dragging the at least one projection image on the display with a user interface device; and
   moving the treatment couch to position the patient based on position adjustments of the at least one projection image.

2. The computer-implemented method of claim 1, wherein the projection images are generated from x-ray images.

3. The computer-implemented method of claim 1, wherein the projection images are generated from fluoroscopy images.

4. The computer-implemented method of claim 1, wherein the synthetic projection image is a digitally reconstructed radiograph.

5. The computer-implemented method of claim 1, wherein displaying at least one of the plurality of projection images comprises:
   displaying a first projection image with a first corresponding synthetic projection image; and
   displaying a second projection image with a second corresponding synthetic projection image.

6. The computer-implemented method of claim 5, wherein the first projection image and the second projection image are a stereo pair of images.

7. The computer-implemented method of claim 1, wherein dragging the at least one projection image comprises:
   moving the at least one projection image with the user interface device to align one or more structures visible in the at least one projection image with a corresponding one or more structures visible in the corresponding synthetic projection image.

8. The computer-implemented method of claim 7, wherein the one or more structures is at least one of an anatomical feature, a fiducial, and a tumor.

9. The computer-implemented of claim 1, wherein moving the treatment couch based on position adjustments of the at least one projection image comprises:
   computing a back projection on the plurality of projection images onto a three dimensional space; and
   positioning the patient in approximate alignment with an imaging center based on the back projection.

10. The computer-implemented method of claim 1, further comprising:
    receiving an input from the user that the at least one projection image has been moved to approximately align with the corresponding synthetic projection image.

11. A computer-readable storage medium having instructions stored thereon that, when executed by a treatment delivery system, cause the treatment delivery system to perform a method, comprising:
    receiving a plurality of projection images of a patient positioned on a treatment couch;
    displaying at least one of the plurality of projection images with a corresponding synthetic projection image on a display;
    adjusting the position of the at least one projection image on the display in response to a user dragging the at least one projection image on the display with a user interface device; and
    transmitting treatment couch positioning data based on position adjustments of the at least one projection image.

12. The computer-readable storage medium of claim 11, wherein the projection images are generated from one of: x-ray images and fluoroscopy images.

13. The computer-readable storage medium of claim 11, wherein displaying at least one of the plurality of projection images comprises:
    displaying a first projection image with a first corresponding synthetic projection image; and
    displaying a second projection image with a second corresponding synthetic projection image.

14. The computer-readable storage medium of claim 11, wherein dragging the at least one projection image comprises:
    moving the at least one projection image with the user interface device to align one or more structures visible in the at least one projection image with a corresponding one or more structures visible in the corresponding synthetic projection image.

15. The computer-readable storage medium of claim 11, wherein transmitting treatment couch positioning data based on position adjustments of the at least one projection image comprises:
    computing a back projection on the plurality of projection images into a three dimensional space; and
    transmitting alignment data to align the treatment couch with an imaging center based on the back projection.

16. A treatment delivery system comprising:
    a display;
    a user interface device;
    a memory; and
    a processing device operatively coupled with the display, the user interface device and the memory to
      obtain a plurality of projection images of a patient positioned on a treatment couch;
      display at least one of the plurality of projection images with a corresponding synthetic projection image on the display;
      adjust the position of the at least one projection image on the display in response to a user dragging the at least one projection image on the display with a user interface device; and
      move the treatment couch based on position adjustments of the at least one projection image.

17. The treatment delivery system of claim 16, wherein the projection images are generated from one of: x-ray images and fluoroscopy images.

18. The treatment delivery system of claim 16, wherein the processing device is to display at least one of the plurality of projection images by:
    displaying a first projection image with a first corresponding synthetic projection image; and displaying a second projection image with a second corresponding synthetic projection image.

19. The treatment delivery system of claim 16, wherein dragging the at least one projection image comprises:
moving the at least one projection image with the user interface device to align one or more structures visible in the at least one projection image with a corresponding one or more structures visible in the corresponding synthetic projection image.

20. The treatment delivery system of claim 16, wherein the processing device is to move the treatment couch based on position adjustments of the at least one projection image by:
computing a back projection on the set of projection images into a three dimensional space; and
aligning the treatment couch with an imaging center based on the back projection.

* * * * *